(12) United States Patent  
Kendall

(10) Patent No.: US 7,072,445 B2
(45) Date of Patent: * Jul. 4, 2006

(54) CONTROLLING COOLING AIR IN CT SYSTEM

(75) Inventor: Charles B. Kendall, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 82 days.

This patent is subject to a terminal disclaimer.

(21) Appl. No.: 10/448,907

(22) Filed: May 30, 2003

(65) Prior Publication Data

US 2004/0240625 A1    Dec. 2, 2004

Related U.S. Application Data

(60) Provisional application No. 60/472,658, filed on May 22, 2003.

(51) Int. Cl.
    *H01J 35/10*     (2006.01)

(52) U.S. Cl. .......................... 378/141; 378/4; 378/199
(58) Field of Classification Search .............. 378/4–20, 378/141, 199
    See application file for complete search history.

(56) References Cited

U.S. PATENT DOCUMENTS

| 5,610,968 | A | * | 3/1997 | Deucher et al. ............ 378/199 |
| 5,956,383 | A | * | 9/1999 | Kendall ....................... 378/199 |
| 6,709,156 | B1 | * | 3/2004 | Hell et al. .................. 378/199 |
| 6,963,632 | B1 | * | 11/2005 | Kendall ....................... 378/141 |

* cited by examiner

*Primary Examiner*—Edward J. Glick
*Assistant Examiner*—Jurie Yun
(74) *Attorney, Agent, or Firm*—Peter Vogel

(57) ABSTRACT

A heat exchanger, together with one or more associated fans, is positioned on the rotating gantry frame in order to cool the x-ray tube of a CT imaging system. An air deflector is positioned on or adjacent to the heat exchanger in order to prevent recirculatoin of heated air in the ganty.

9 Claims, 4 Drawing Sheets

CONTROLLING COOLING AIR IN CT SYSTEM

CROSS-REFERENCE TO RELATED APPLICATIONS

This case is related to the subject matter as set forth in Provisional Patent Application Ser. No. 60/472,658 filed on May 22, 2003.

TECHNICAL FIELD

The present invention relates generally to CT imaging systems, and more particularly to imaging systems that use fans and heat exchangers as part of the cooling systems.

BACKGROUND OF THE INVENTION

Computed tomography (CT) imaging systems are in wide use today. The CT systems include a gantry that rotates in order to create a 360° image. The gantry icludes an x-ray tube as well as a cooling system to control the temperature of the x-ray tube. The cooling system typically employs a liquid-to-air heat exchanger to remove heat from the x-ray tube during operation. The cooling system also typically includes one or more fans that are used to draw or force air through the heat exchanger and exhaust heated air from the gantry.

The size and surface area of the heat exchanger required in a particular application is partly a function of the power to be dissipated, and the temperature of the ambient air sent through the heat exchanger. On high power CT systems, the ambient air temperature in combination with the higher power requirements often makes the packaging difficult for large heat exchangers.

Also, the rotating gantry is normally encased in a tight fitting cover system, and the cooling air drawn into the heat exchanger is normally supplied by air that is already present in the gantry during operation. The temperature of the cooling air increases as it absorbs heat from the liquid flow to the heat exchanger. The heated air is then expelled from the heat exchanger. Although the heated air is directed to vents in the gantry structure, not all of the air typically exits from the gantry due to the tight spacing between the rotating heat exchanger and the stationary gantry cover. This often allows for above-ambient temperature air to recirculate and be re-ingested into the heat exchanger. This can result in the x-ray tube oil stabilizing at an elevated temperature and possibly reducing the thermal performance of the system.

It would, therefore, be desirable to reduce the amount of heated air that is re-ingested into the heat exchanger and thus improve the thermal performance of the system.

SUMMARY OF THE INVENTION

It is an object of the present invention to provide an improved heat exchanger for the cooling system of a CT imaging system. It is a another object of the present invention to provide an improved cooling system for a CT imaging system which reduces the ingestation of previously heated air.

It is a further object of the present invention to provide a cooling system for a CT imaging system which forces the air drawn into the heat exchanger to come from the inboard regions of the gantry. It is a still additional object of the present invention to provide a cooling system for a CT imaging system that improves the thermal performance of the CT system.

These and other objects of the present invention are accomplished by the method apparatus and system set forth in the accompanying specification, drawings, and claims. In addition, the present invention has many benefits and advantages over known apparatus, methods and systems which are used to cool X-ray tubes in CT imaging systems.

In accordance with the present invention, the heat exchanger for the cooling system is preferably shaped and provided to fit within as much of the allowable space as possible in the gantry. The heat exchanger is positioned adjacent the x-ray tube on the rotating gantry and has one or more fans operably associated with it. The gantry has a cover or outer structure that fits over the rotating components and often has an annulus or "doughnut" shape. Regardless of the actual shape of the cover, it typically has a surface which is positioned close to the rotating components.

In accordance with the present invention, an air deflector is mounted on the rim or edge of the heat exchanger. The deflector extends over the face of the heat exchanger and forces air drawn into the heat exchanger to come from the inboard regions of the gantry where cooler air is located. This reduces the ingestion of previously heated air and allows the x-ray tube oil to run at low or nominal temperature. This results in reduced operating temperatures and increase thermal performance of the CT system.

Other aspects and advantages of the present invention will become apparent upon the following detailed description and appended claims, and upon reference to the accompanying drawings.

BRIEF DESCRIPTION OF THE DRAWINGS

For a more complete understanding of the invention, reference can be made to the embodiments illustrated in greater detail in the accompanying drawings and described below by way of examples.

DESCRIPTION OF THE PREFERRED EMBODIMENT(S)

Figure 1:
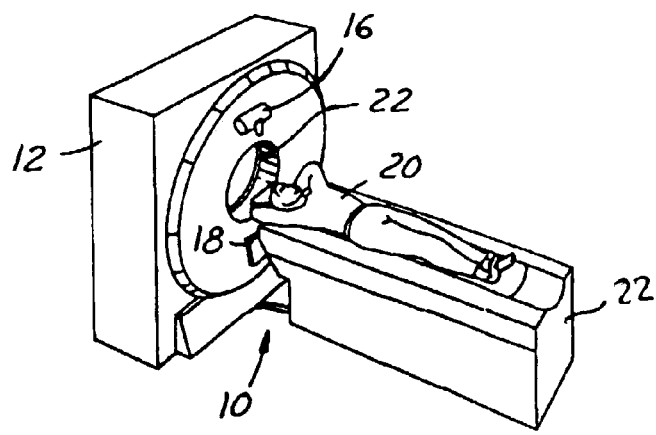
FIG. 1 is a schematic illustration of a CT system illustrating its general components.

In each of the following figures, the same reference numerals are used to refer to the same components. Also, while the present inventions are described with respect to apparatuses, systems, and methods of improving cooling systems for computed tomography (CT) imaging systems, the present inventions are capable of being adapted for various purposes are not limited strictly to CT systems. For example, the present inventions can be utilized in MRI systems, radio therapy systems, other x-ray imaging systems, ultrasound systems, nuclear imaging systems, magnetic resonant spectroscopy systems, and other applications and systems known in the art.

Also, although the present invention is described as being used in connection with x-ray tubes for CT imaging systems, the present invention can be used in conjunction with other imaging tubes, including vascular tubes.

In the following description, various operating parameters and components are described for preferred embodiments of the present invention. The specific parameters and embodiments are included only as examples and are not meant to be limiting.

Referring now to FIG. 1, a schematic illustration of a conventional computed tomography (CT) system is disclosed and referred to generally by the reference numeral 10. The imaging system 10 includes a gantry 12 that has an x-ray imaging tube 16. The imaging tube 16 projects a beam of x-rays toward a detector array 18.

When the CT imaging system is utilized, a patient 20 positioned on a movable slider tray mechanism 22 is positioned in the central bore 22. X-rays from the imaging tube 16 pass through the patient within the bore 22 and are detected by the detector array 18 and used to create a CT image or a construction.

Figure 2:
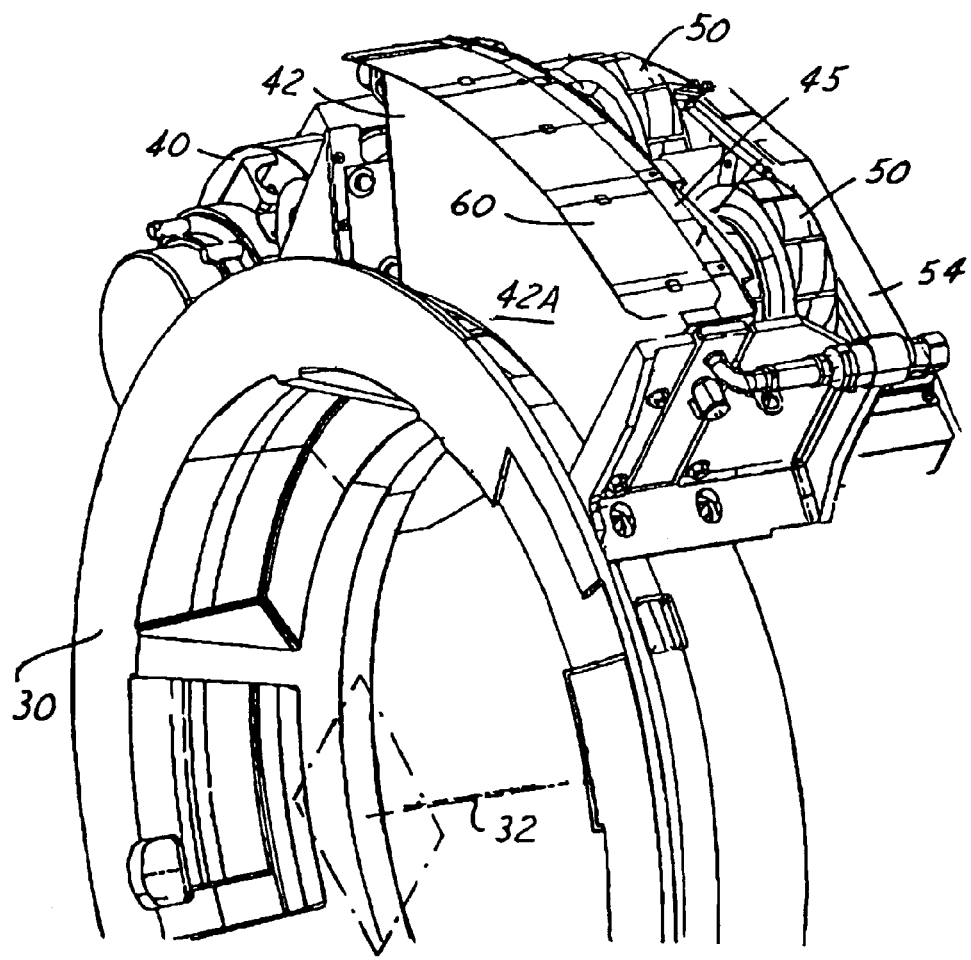
FIG. 2 illustrates a portion of the gantry system including a heat exchanger and deflector in accordance with the present invention.

FIG. 2 illustrates several of the inner components of the gantry member 12. The gantry has an outer cover or structure 13 and a rotating inner annular frame member 30 which rotates about a gantry axis 32. The frame member 30 has a number of components attached to it and which rotate with it. These components include an x-ray tube 40, a heat exchanger 42, one or more fan members 50, two of which are shown in FIG. 2, and a fan mounting bracket 54. The cover 13 has at least one surface which is positioned relatively tight close to the cooling system components as they are rotated inside the cover. Typically, the clearance is about 0.50 inches to about 6.0 inches.

The CT system illustrated is simplified to highlight the aspects of the present invention. Those skilled in the art will recognize various other components that need to be present and included in such systems. For example, CT system 10 also includes a controller which is preferably micro-processor based. The controller is designed to control the operation of the cooling system for the x-ray tube 40.

The cooling system includes as its principal components, the heat exchanger 42 and the fans 50. In this regard, the heat exchanger 42 is preferably an oil-to-air heat exchanger and is also commonly called an "oil cooler." Liquid-to-air types of heat exchangers are typically used in x-ray systems. Also, in the embodiment shown in the drawings, the fans 50 are integrally coupled to the heat exchanger 42. Persons skilled in the art will recognize that one or more fans may be separate components placed adjacent to the heat exchanger.

The cooling fans 50 are designed to help move air through the heat exchanger to cool the liquid circulating in the heat exchanger and ultimately the x-ray tube 40. A controller (not shown) is operably coupled to the fans to control their speed and thus control the amount of cooling in the system. In this regard, the speed of the fan preferably varies over the operating temperature range of the x-ray tube. When a predetermined temperature is reached, such as 100° F., the fan speed is elevated to maintain a maximum fan speed. The maximum fan speed could be, for example, 2900 rpm. Also, the output of the controller and thus the operation of the fan does not necessarily have to be linear.

An air deflector 60 is also shown in FIG. 2. An air deflector (a/k/a "visor") is attached to the heat exchanger 42 and extends over the front face 42A thereof. In this regard, air passing through the heat exchanger is introduced into the exchanger through front surface 42A and thus is pulled through the heat exchanger by the fans 50.

Figure 3:
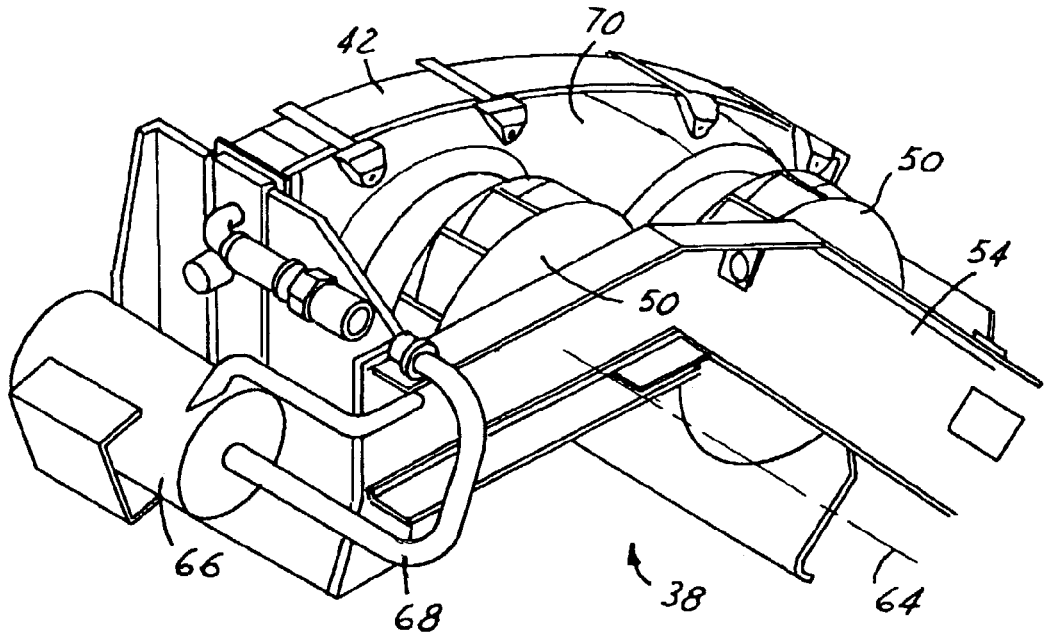
FIG. 3 illustrates a preferred heat exchanger that can be used with the present invention.

Another embodiment of a heat exchanger is shown in FIG. 3. As shown, the fan axis 64 is parallel to the gantry axis 32. This is the preferred orientation of the air flow and fan rotation in accordance with the present invention. In this manner, the fans 50 which are associated with the heat exchanger 42, are oriented with their rotational axis parallel to their rotational axis of the gantry. This eliminates gyroscopic loading on the fan shaft when the fan axis and gantry axis are not in parallel.

The cooling system is generally referred to by reference numeral 38 in FIG. 3 and also includes a pump 66 and a shroud member 70. The pump 66 is used to circulate cooling oil through conduit 68 into and out of the heat exchanger 42. The shroud 70 is used to direct air passing through the heat exchanger through the fans 50.

Figure 4:
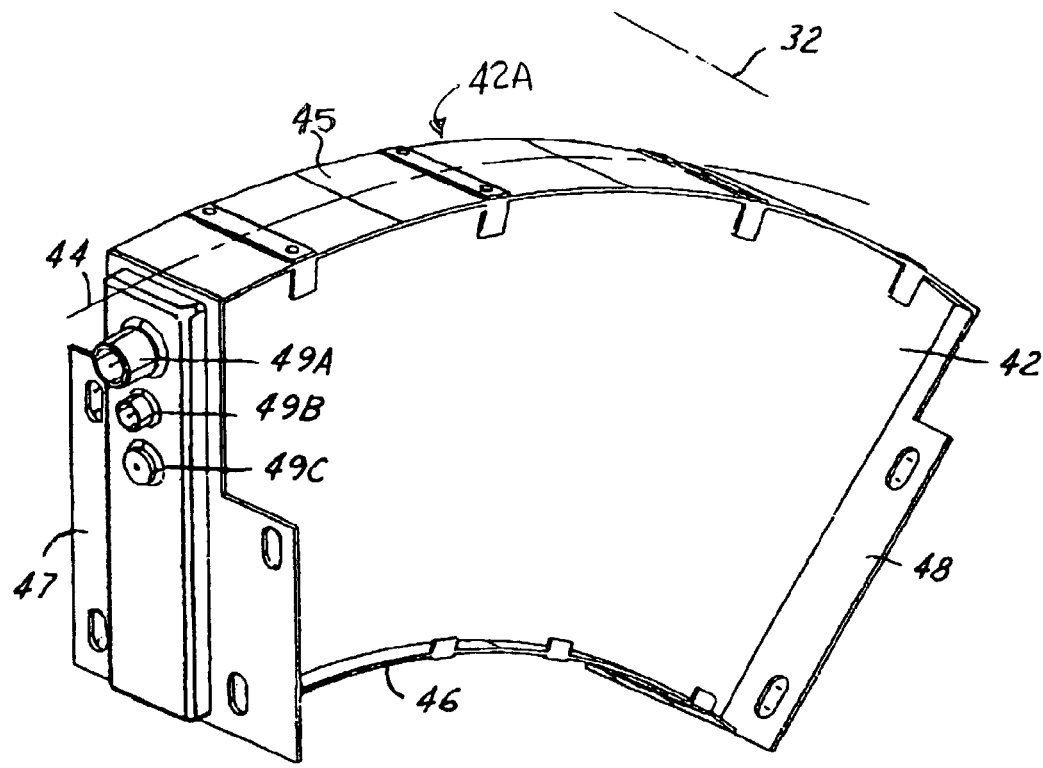
FIGS. 4, 5, and 6 are various views of a preferred heat exchanger that can be utilized with the present invention.
Figure 5:
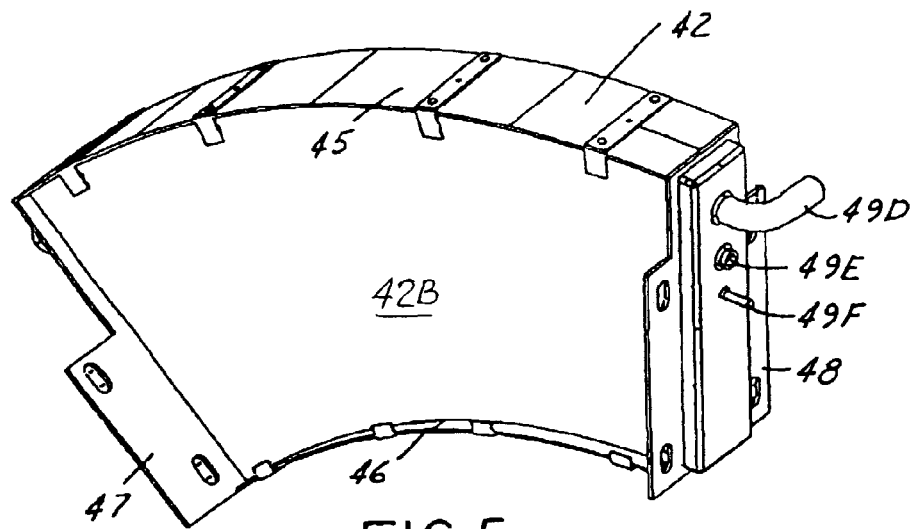
Figure 6:
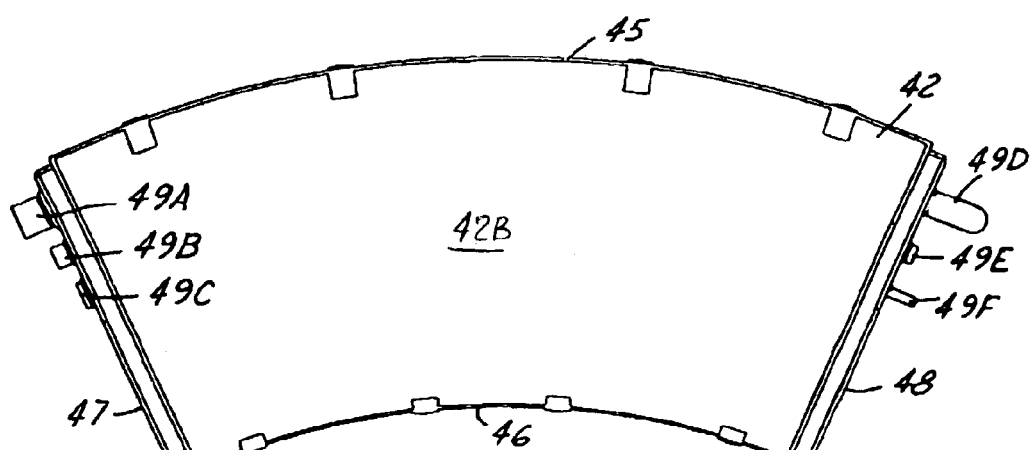

A preferred shape of the heat exchanger 42 is shown in FIGS. 4, 5, and 6. In this embodiment, the heat exchanger 42 is formed in the shape of a sector of an annulus and has a curvature 44 that matches the rotating envelope of the CT gantry. The curved shape of the heat exchanger presents a larger surface area for dissipating heat from the gantry and CT imaging system. There is a limited amount of space available in the tight fitting cover of the rotating gantry in conventional CT imaging systems. Conventional heat exchangers are typically rectangular in shape and are limited in order to allow the heat exchanger to fit within the available space.

In this regard, although the present invention is shown mounted on a curved heat exchanger, it is to be understood that the inventive air deflector can be utilized with any heat exchanger, regardless of the size or shape. Also, although maintenance of an axial air flow through the heat exchanger and through the gantry is preferred, it is also possible to utilize the invention relative to heat exchangers which are positioned in other orientations, or with fans which are not oriented with their axis parallel to the gantry axis.

In the heat exchanger shown in FIGS. 4–6, the device has supporting and/or mounting members on the four perimeter surfaces. For example, curved brackets 45 and 46 are positioned on the upper and lower perimeter surfaces, respectively, of the heat exchanger 42, while mounting brackets 47 and 48 are positioned on the two end perimeter surfaces. The end mounting brackets 47 and 48 also contain various hardware for inflow and outflow of the oil through the coils inside the heat exchanger (not shown). This hardware is referred to generally by the reference numerals 49A–49F.

Figure 7:
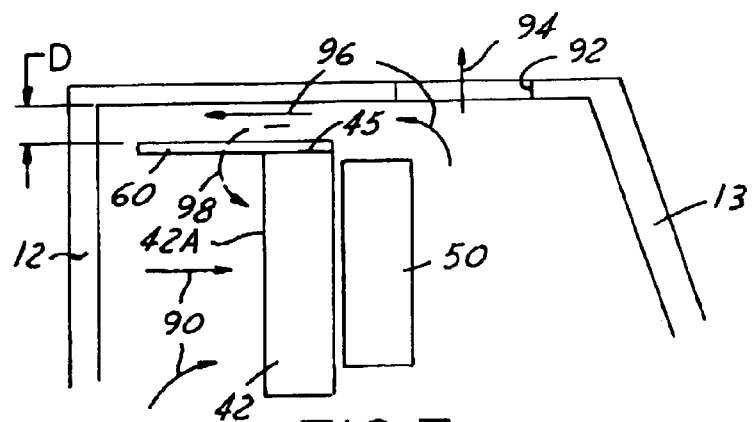
FIG. 7 is a schematic diagram illustrating the use of an inventive deflector member in accordance with the present invention.

FIG. 7 schematically illustrates an air deflector 60 for use in the present invention, and also illustrates the affect of the air flow inside the gantry when the deflector is utilized. As indicated, the air deflector or visor 60 is preferably positioned on and attached to the top of the heat exchanger 42. Cooler inlet air represented by arrow 90 is pulled into and through the heat exchanger 42 by the fan 50, which is positioned immediately behind the heat exchanger. The air which passes through the fan 50 is supposed to exit the gantry structure 13 through the air vent 92 as represented by arrow 94.

However, as shown in FIG. 7, a portion of the heated air is typically recirculated inside the cover 13 of the gantry in a direction toward the front surface 42A of the heat exchanger 42. This recirculated air is indicated by arrows 96. Without the air deflector 60 in place, the recirculated air which is at an elevated temperature would follow the path of the arrow 98 which is shown in dotted lines and would be passed back through the heat exchanger and fan.

Cooling air drawn into the heat exchanger is normally supplied by air that is already present in the gantry during operation. The cooling air temperature increases as it absorbs heat from the tube oil flowing through the heat exchanger 42. The heated air is then preferably expelled from the heat exchanger through air vent 92. When the gantry is brought to a stationary position, the heated exit air is directed to the air vents 92 on the gantry cover or structure 13. However, in conventional CT systems, not all of the air exits from the gantry due to the close spacing between the gantry cover 13 and the rotating cooling system components. Without the air deflector 60, this would allow above-ambient temperature air to recirculate and he reingested into the heat exchanger. When this happens, the x-ray tube oil can stabilize at an elevated temperature and reduce the thermal performance of the system. The present air deflector 60 reduces the ingestion of previously heated air and forces the air going into the heat exchanger to come from the inboard regions of the gantry. The invention allows for the x-ray tube oil to run at a lower nominal temperature resulting in increased thermal performance of the CT system.

As indicated, the air deflector 60 preferably is mounted directly on the upper bracket or surface 45 of the heat exchanger 42. This is shown in FIG. 2, as well as FIG. 8. However, it is also possible for the air deflector to be mounted at other locations, such as the front surface 42A of the heat exchanger, the end perimeter surfaces, one or more of the mounting brackets associated with the cooling system 38, or the inside of the cover structure 13, etc. so long as it can perform the function of preventing at least a portion of the heated air from being reingested into the heat exchanger. The size, shape, and location of the air deflector can be dependent on many factors, including the type of CT system utilized, the shape of the cover structure, and the like.

Figure 8:
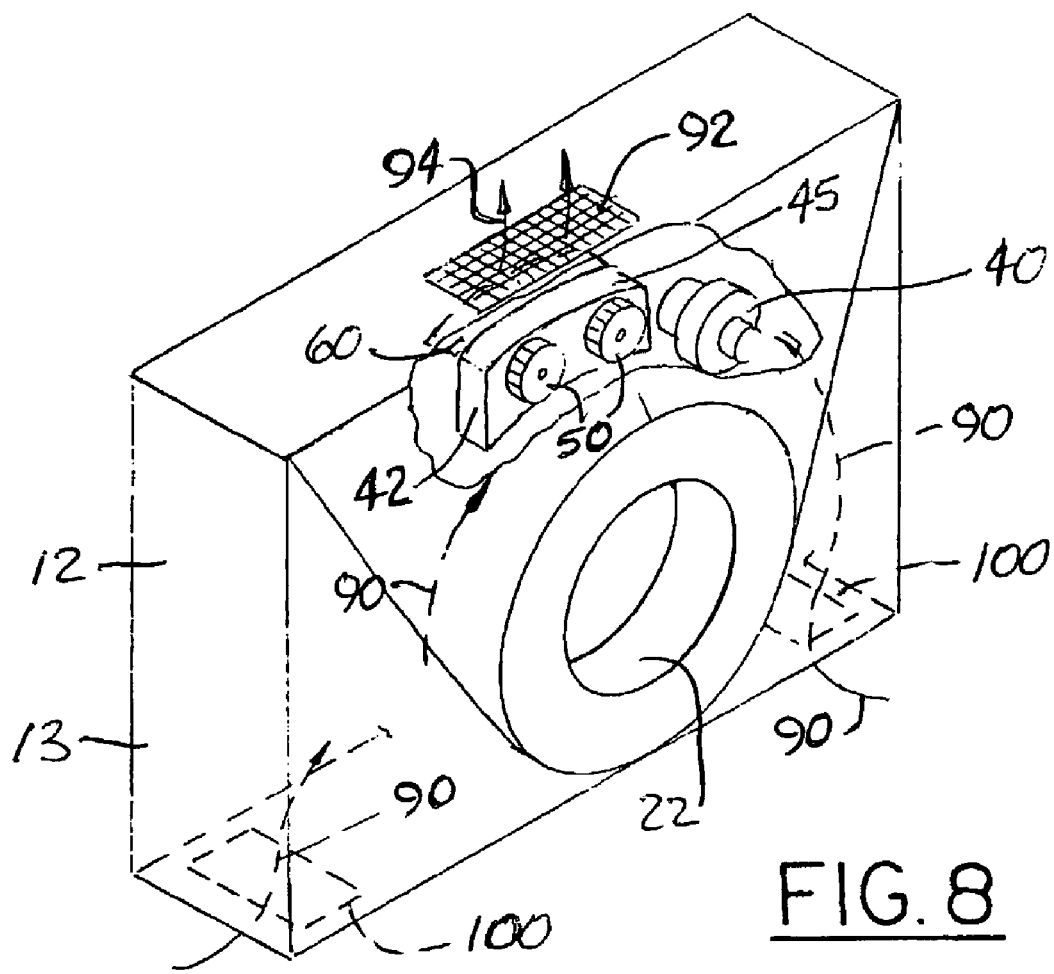
FIG. 8 is a schematic diagram illustrating a heat exchanger and deflector member in accordance with an embodiment of the present invention.

FIG. 8 is another schematic view of a gantry and cooling system in accordance with the present invention. As illustrated, cool inlet air 90 is drawn up through the gantry cover structure 12 through air vents 100 positioned in the lower portions of the cover structure 13. The cooled inlet air is then directed toward the front surface 42A of the heat exchanger 42 as schematically shown in FIG. 7. The heat exchanger and fans are positioned to allow air flow parallel to the gantry axis and an air deflector 60 is mounted as a visor on the heat exchanger.

While particular embodiments of the invention have been shown and described, numerous variations and alternative embodiments will occur to those skilled in the arm. Accordingly, it is intended that the invention be limited only in terms of the appended claims.

What is claimed is:

1. A computed tomography (CT) imaging system comprising a gantry member, said gantry member having a rotating frame member;
   an x-ray tube positioned on said frame member;
   a heat exchanger positioned on said frame member adjacent said x-ray tube and adapted to cool said x-ray tube;
   at least one fan member positioned adjacent said heat exchanger and adapted to flow air through said heat exchanger; and
   an air deflector member positioned on said heat exchanger for preventing recirculation of heated air through said fan member;
   said heat exchanger having an upper perimeter surface, a lower perimeter surface, a first end perimeter surface and a second end perimeter surface, and said air deflector member being positioned on said upper perimeter surface;
   said upper perimeter surface and said lower perimeter surface each having a curved configuration;
   said air deflector member having a curved configuration substantially the same as said curved configuration of said upper perimeter surface and positioned to extend in a direction substantially parallel to the axis of rotation of said fan member.

2. The computed tomography (CT) imaging system as described in claim 1 further comprising a shroud positioned between said heat exchanger and said at least one fan member.

3. The computer tomography (CT) imaging system as described in claim 1 wherein said gantry member has a first axis of rotation and said fan member has a second axis of rotation, said first and second axes of rotation being substantially parallel to one another.

4. A computer tomography (CT) imaging system as described in claim 1 wherein said heat exchanger has at least one substantially planar side surface and said fan member has an axis of rotation, and wherein said axis of rotation is substantially perpendicular to said planar side surface.

5. A computer tomography (CT) imaging system as described in claim 4 wherein two of said fan members are provided, each of said fan members having an axis of rotation substantially perpendicular to said planar surface.

6. A computer tomography (CT) imaging system as described in claim 1 wherein at least one of said first and second end perimeter surfaces has a mounting bracket thereon, and wherein at least one of said first and second end perimeter surfaces has at least one liquid fixture thereon.

7. The computer tomography (CT) imaging system as described in claim 1 wherein said heat exchanger is a liquid-to-air type heat exchanger.

8. The computed tomography (CT) imaging system as described in claim 7 wherein said liquid is an oil material.

9. The computed tomography (CT) imaging system as described in claim 1 further comprising a cover member covering said rotating frame member, x-ray tube, heat exchanger, and air deflector member, said cover member having at least one surface which is spaced a distance of 0.50 to 6.0 inches from said heat exchanger.

* * * * *